United States Patent [19]
Lotz et al.

[11] Patent Number: 5,271,931
[45] Date of Patent: Dec. 21, 1993

[54] METHODS FOR INCREASING C1 INHIBITOR CONCENTRATIONS USING INTERFERON-GAMMA AND/OR INTERLEUKIN-6

[75] Inventors: Martin Lotz, San Diego; Bruce Zuraw; Dennis A. Carson, both of Del Mar, all of Calif.

[73] Assignee: The Scripps Research Institute, La Jolla, Calif.

[21] Appl. No.: 244,265

[22] Filed: Sep. 14, 1988

[51] Int. Cl.$^5$ ............................................. A61K 37/66
[52] U.S. Cl. ................................. 424/85.5; 424/85.1; 424/85.2; 424/85.4; 424/85.6; 604/4
[58] Field of Search .................... 424/85.1, 85.2, 85.5, 424/85.6, 85.4; 604/4

[56] References Cited

PUBLICATIONS

Fong et al., *J. Immunmol.*, 142, 1989, pp. 2321-2324.
Jones et al., *Biochem. Soc. Transactions*, vol. 15, 1987, p. 638.
Hack et al., *Blood*, 74(5) 1989, pp. 1704-1710.
Neta et al., *Lymphokine Res.* 7(1) 1988, pp. 403-412.
Katz et al., *J. Immunol.*, 1989, vol. 142(6) pp. 2041∝2045.
Katz et al., *Arthritis Rheum*, 31(11) 1988, pp. 1365-1370.
Lotz et al., *J. Immunol.*, 139, 1987, pp. 3382-3387.
Lotz et al., *J. Allerg Clin Immunol*, 79, 1987, p. 194, A280.
Lappin et al., Complement 4:184, A160, 1987.
Hamilton et al., *Biochem J.*, 242, 1987, pp. 809-815.
Zuraw et al., Complement, 4:44, A319, 1987.
Davis et al., *Ann. Rev. Immunol.*, 6:595-628 (1988).
Proud et al., *Ann. Rev. Immunol.*, 6:49-83 (1988).
Zuraw et al., *J. Clin. Invest.*, 78:567-575 (1986).
Zuraw et al., *J. Allerg. Clin. Immunol.*, 81:223, A218 (1988).
Zuraw et al., *J. Allerg. Clin. Immunol.*, 73:155, A185 (1984).
Johnson et al., *Science*, 173:553-554 (1971).
Lotz et al., *J. Immunol.*, 136:3636-3642 (1986).
Firestein et al., *Arthrit. Rheum.*, 30:S115, E13 (1987).
Nitsche et al., *Am. J. Clin. Path.*, 76(5):679-684 (1981).
Lockshin et al., *Arthrit. Rheum.*, 29:1467-1472 (1986).
Lewin et al., *J. Biol. Chem.*, 258:6415-6421 (1983).
Kaplan et al., *Blood*, 66:636-641 (1985).
Berrettini et al., *Blood*, 68:455-462 (1986).
Hugli et al., "Techniques and Significance of C3a and C5a Measurement", in *Immunoassays: Clinical Laboratory Techniques for the 1980s*, Nakamura et al., eds., Alan R. Liss, New York, pp. 443-460 (1980).
Kozin et al., "The Contact Activation System of Plasma", in *Inflammation: Basic Principles and Clinical Correlates*, Gallin et al., eds., Raven Press, Ltd., pp. 101-120 (1988).
Chenoweth et al., *N. Engl. J. Med.*, 304:497-503 (1981).
Scott et al., *Blood*, 63:42-50 (1984).
Saito, *Semin. Thromb. Hemostasis*, 13:36-49 (1987).
Gray et al., *Nature*, 295:503-508 (1982).
Zoon et al., *Proc. Natl. Acad. Sci. USA*, 76:5601-5606 (1979).
Knight et al., *Science*, 207:525-526 (1980).
Stein et al., *Proc. Natl. Acad. Sci. USA*, 77:5716-5619 (1980).
Goeddel et al., *Nucleic Acids Res.*, 8:4057-4073 (1980).
Hitzeman et al., *Nature*, 293:717-722 (1981).
Muraguchi et al., *J. Immunol.*, 127:412-416 (1981).
Kalter et al., *J. Infect. Dis.*, 151:1019-1027 (1985).
Gelfand et al., *Medicine*, 58:321-328 (1979).
Frank et al., *Ann. Int. Med.*, 84:580-593 (1976).
Arroyave et al., *J. Immunol.*, 177:1866-1869 (1976).
Fareed et al., *Sem. Thromb. Hemostasis*, 10:306-328 (1984).
Salvesen et al., *J. Biol. Chem.*, 260:2432-2436 (1985).
Laemmli et al., *Nature*, 277:680-685 (1970).

*Primary Examiner*—Garnette D. Draper
*Attorney, Agent, or Firm*—Douglas A. Bingham; Thomas Fitting; April C. Logan

[57] ABSTRACT

The present invention relates to the use of interferon and/or interleukin-6 to increase intravascular C1 inhibitor concentrations in patients exhibiting or at risk for a C1 inhibitor deficiency. Therapeutic compositions containing interferon and/or interleukin-6 are also disclosed.

8 Claims, 3 Drawing Sheets

METHODS FOR INCREASING C1 INHIBITOR CONCENTRATIONS USING INTERFERON-GAMMA AND/OR INTERLEUKIN-6

This invention was made with government support under National Institutes of Health Contract Nos. RR00833-10S2, AI10386, and AR21175. The government has certain rights in the invention.

TECHNICAL FIELD

The present invention relates to the use of human interferon and/or interleukin-6 to increase intravascular C1 inhibitor concentrations in patients either exhibiting or at risk for C1 inhibitor deficiencies.

BACKGROUND

C1 inhibitor (C1INH) is a serine protease inhibitor involved in the regulation of several proteolytic systems in plasma including the complement, contact, coagulation and fibrinolytic systems. Davis et al., *Ann. Rev. Immunol.*, 6:595-628 (1988). C1INH is known to regulate those systems by forming covalent complexes with specific serine protease components of each system.

Several specific serine proteases whose activity are directly regulated by C1 inhibitor have been identified. For instance, C1INH is the only known inhibitor of C1r and C1s, both of which are activated fragments of the complement system component C1.

In addition, the art teaches that C1INH is the most important inhibitor of the contact system because C1INH is the primary inhibitor of both kallikrein and the activated forms of coagulation factor XII, including factor XIIa and factor XIIf (Hageman factor). Proud et al., *Ann. Rev. Immunol.*, 6:49-83 (1988).

Deficiencies in C1INH are known to cause serious and potentially life-threatening diseases. The best characterized example of a C1INH deficiency is found in individuals with hereditary angioedema (HAE), also known as hereditary angioneurotic disorder, caused by a hereditary deficiency in the ability to produce C1INH. Individuals with symptoms of HAE exhibit recurrent, acute, local circumscribed edema of the skin or mucosa, primarily on the extremities, face, larynx and gastrointestinal tract. Davis et al., *Ann. Rev. Immunol.*, 6:595-628 (1988).

Another distinct type of C1INH deficiency, termed acquired C1INH deficiency, occurs in individuals who synthesize normal amounts of C1INH, but cannot maintain sufficient concentrations of the inhibitor because of its increased catabolism. Individuals with acquired C1INH deficiency exhibit the symptoms of HAE. Whereas both HAE and acquired C1INH deficiency exhibit the typical laboratory profile of decreased levels of both C1INH and complement system components C4 and C2, the levels of complement system component C1q is decreased only in the acquired disease.

Presently, three distinct mechanisms have been proposed that create an acquired C1INH deficiency. First, a C1INH deficiency can be acquired when the amount of normally available C1INH is consumed by an excessive amount of complement and/or contact system activation. Some of the activated components of each of the complement and contact systems can bind and inactivate C1INH. In addition, activated contact system components can cleave C1INH into inactive fragments. Zuraw et al., *J. Clin. Invest.*, 78:567-575 (1986).

Second, a C1INH deficiency can be acquired as the result of an anti-C1INH autoimmune reaction. In such a case, C1INH is synthesized, but anti-C1INH autoantibodies bind the inhibitor and thereby prevent its ability to regulate serine protease activity. Third, a C1INH deficiency can be acquired as a result of C1INH being bound by complement-containing autoimmune complexes which are rapidly cleared from the circulation.

From the foregoing, it can be seen that a method for increasing the intravascular level of C1INH would be useful for treating disease caused by C1INH deficiencies. A method for increasing intravascular C1INH concentrations would be particularly useful as a prophylactic treatment for C1INH consumption due to acute complement and/or contact system activation.

Presently, the specific physiological mechanism(s) controlling the blood concentration of C1INH is not known. The primary site of C1INH synthesis during the acute phase reaction to blood trauma has been proposed to be the liver. Davis et al., *Ann. Rev. Immunol.*, 6:595-628 (1988); Johnson et al., *Science*, 173-553-554 (1971). *Complement*, 4:244, A319 (1987). In contrast, the source of C1INH in response to localized, non-traumatic inflammation appears to be cells of the monocycle/macrophage lineage. For instance, several in vitro studies have suggested that cultured monocytes can be stimulated to synthesize C1INH by treatment with interferon gamma. See, Hamilton et al., *Biochem. J.*, 242:809-815 (1987); Lotz et al., *J. Immunol.*, 139:3382-3387 (1987); Lotz et al., *J. Allerg. Clin. Immunol.*, 79:194, A280 (1987); and Lappin et al., *Complement*, 4:184, A160 (1987). In addition, the results of one in vitro study suggest that cultured hepatocytes synthesize C1INH in response to interferon gamma. Zuraw et al., *Complement*, 4:244, A319, 1987).

However, as is well known in the art, the results of in vitro studies obtained with interferon gamma do not predictably indicate that the same results will be obtained in vivo. For example, the treatment of cultured monocytes with interferon gamma results in an increase in the level of HLA-DR antigen expression on the surface of the monocytes. In contrast, administration of interferon gamma to a patient decreased the level of HLA-DR antigen expression by monocytes in the patient. Firestein et al., *Arthrit. Rheum.*, 30:S115, E13 (1987).

To date there has been no study of interferon gamma's effects on C1INH levels in vivo. This is not surprising in view of the fact that interferon gamma, as it is presently understood, is described as an immunomodulator that regulates activation and growth of specific immune cells.

BRIEF SUMMARY OF THE INVENTION

It has now been found that administration of interferon gamma and/or interleukin-6 (IL-6) increases the intravascular concentration of C1 inhibitor.

Therefore, the present invention contemplates a palliative treatment for blood trauma in a patient, which method comprises administering to the patient a C1 inhibitor concentration-increasing amount of interferon and/or IL-6.

In another embodiment, the present invention contemplates a therapeutic method in which blood of a patient circulates through a prosthetic device, which method includes administering a C1 inhibitor concentration-increasing amount of interferon and/or IL-6 to the patient substantially concurrently with exposing the patient's blood to a prosthetic surface on the device.

Also contemplated is a palliative treatment for surgically induced blood trauma, which treatment comprises administering a C1 inhibitor concentration-increasing amount of interferon to a patient substantially concurrently with performing an invasive surgical procedure on the patient.

Further contemplated is a method of increasing the intravascular concentration of C1 inhibitor in a patient exhibiting a clinical symptom of C1 inhibitor deficiency, which method includes administering to the patient a therapeutically effective amount of interferon and/or IL-6.

DETAILED DESCRIPTION OF THE INVENTION

Figure 1:
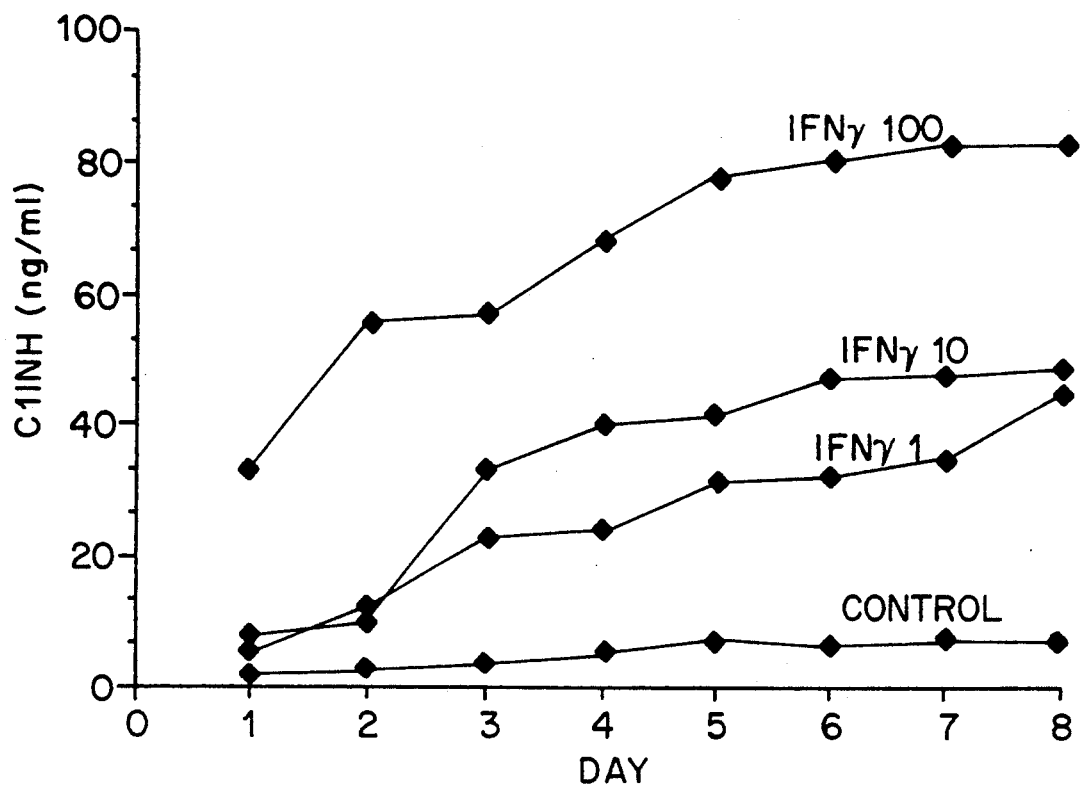
FIG. 1 is a graph illustrating the in vitro dose dependent effect of gamma interferon stimulation on C1INH secretion. HepG2 cells were stimulated by addition to the culture medium of varying amounts, from 1 international unit (IU) per ml (IFN 1) to 100 IU per ml (IFN 100), of interferon gamma, as described in Example 3A. A control culture was maintained that received no interferon gamma. Culture supernatant samples were removed at the days indicated and the level of secreted C1INH was determined by ELISA assay and expressed as nanograms C1INH per milliliter media (ng/ml).

The present invention contemplates new uses for interferon and IL-6 born out of the discovery that intravenous administration of either or both increases the amount of C1 inhibitor (C1INH) present in a patient's blood.

Thus, the present invention contemplates a method for palliating or preventing blood trauma in a patient comprising administering to the patient a C1 inhibitor concentration-increasing amount of interferon, preferably interferon gamma, or IL-6, or both.

As used herein, the phrase "blood trauma" refers to a physiological state in which the complement system and/or the contact system of a patient's blood are activated to a clinically significant degree, i.e., to a degree that typically produces secondary symptoms such as acute or chronic inflammation, pulmonary edema, vascular hypotension and the like.

Methods for determining the presence of a clinically significant degree of complement system activation in a patient's blood are well known in the art. Those methods typically assay the amount of an activated complement system component For example, the presence of a ratio in the blood of activated complement fragment C4D to non-activated complement component C4 in excess of 1.2 indicates the presence of blood trauma, i.e., a clinically significant degree of complement system activation. See Nitsche et al., Am. J. Clin. Path., 75:679-684 (1981). (The teachings of the art cited herein are incorporated by reference.)

In addition, complement system activation can be determined by detecting increased intravascular concentrations of the activated complement components C1s, C3a or C5a. In one method, the intravascular level of C1s is measured by detecting the amount of C1s:C1INH complex present in a blood sample as described by Lockshin et al., Arthritis Rheum., 29:1467-1472 (1986). Complement system activation is considered clinically significant if the intravascular level of C1s:C1INH complex exceeds 12 nanomoles per milliliter (ml) blood.

The two products of complement activitation, C3a and C5a, are of particular pathophysiological importance. C3a and C5a activate neutrophils, monocytes and basophils to produce oxygen radicals, arachidonic acid metabolites and histamine. In monocytes, C3a and C5a stimulate synthesis of the interleukins 1 and 6 (IL-1 and IL-6) resulting in fever and the hepatic acute phase response. C3a and C5a are therefore critical mediators of the clinical symptoms occurring as the result of blood trauma.

Intravascular levels of C3a and C5a are measured by radioimmunoassay as described by Hugli et al., "Techniques and Signifcance of C3a and C5a Measurement", in Immunoassays: Clinical Laboratory Techniques for the 1980s, Nakamura et al., eds., Alan R. Liss, New York, pp. 443-460 (1980). An assay kit based on the Hugli protocol is commercially available from Upjohn Diagnostics (Kalamazoo, Mich.). Complement system activation is considered clinically significant if the intravascular levels of C3a or C5a exceed 200 ng per ml or 30 ng per ml, respectively, when assayed using the Hugli protocol (suora) as discussed by Chenoweth et al., *N. Engl. J. Med.*, 304:497–503 (1981).

"Contact system activation" refers to the process wherein the components of the contact system, such as coagulation factors XI, XII and pre-kallikrein, become activated. Contact system activation results in the production of potent vasoactive peptides, such as bradykinin, that mediate inflammatory reactions, and control blood flow and blood pressure. Three important activated components of the contact system, kallikrein and coagulation factors XIa and XIIa are generated when their non-activated precursors, pre-kallikrein and coagulation factors XI and XII, respectively, are exposed to a contact system activating surface such as, for example, endothelial basal membrane surfaces or macromolecular anionic surfaces such as those found on synthetic prosthetic surfaces. See, for example Proud et al., *Ann. Rev. Immunol.*, 6:49–83 (1988); and Kozin et al., "The Contact Activation System of Plasma", in *Inflammation: Basic Principles and Clinical Correlates*, Gallin et al., eds., Raven Press, Ltd., P101–120 (1988).

Assays for determining the presence of activated contact system components in a patient's blood, and thus the presence of contact system activation, are well known. For example, C1 inhibitor-kallikrein complexes can be detected by enzyme-linked immunosorbent assay (ELISA) as described by Lewin et al., *J. Biol. Chem.*, 258:6415–6421 (1983). Contact system activation is considered clinically significant when the intravascular level of C1INH-kallikrein complex exceeds about 5 namomolar (nM).

Similarly, C1 inhibitor-factor XIIa complexes can be detected in a patient's blood using ELISA as described by Kaplan et al., *Blood*, 60:636–641 (1985). Contact activation is considered clinically significant when the intravascular level of C1INH-factor XIIa complex is greater than 5 nM. Alternatively, the cleavage of high molecular weight kininogen (HMWK) to form a lower molecular weight cleavage product can be monitored in patient's blood by the immunoblotting procedure of Berrettini et al., *Blood*, 68:455–462 (1986). Because the cleavage of HMWK occurs by the action of the activated contact system component kallikrein, the presence of cleavage product indicates contact system activation. In addition, the processing of C1 inhibitor to a modified form in a patient's blood is indicative of contact system activation. A 94,000 dalton modified C1 inhibitor protein is detectable in a patient's blood by means of an immunoblotting method described by Zuraw et al., *J. Clin. Invest.*, 78:567–575 (1986).

Alternatively, contact system activation can be determined by measuring the coagulant activity of activated factor XI (e.g., XIa) using the amidolytic assay described by Scott et al., *Blood*, 63:42–50 (1984). In that assay, one international unit (IU) of factor XIa is that amount sufficient to hydrolyze 0.49 micromoles of the synthetic substrate PyrGlu-Pro-Arg-p-nitroanalide (S-2366) per min per ml. Contact system activation is considered clinically significant when the intravascular level of factor XIa exceeds 1.5 IU per ml.

In addition, contact system activation can be indicated by the symptoms clinically presented by a patient. For example, the activation of contact system components has been implicated in clinical conditions such as allergic reactions, arthritis, disseminated intravascular coagulation and shock. For a description of those symptoms, see Saito, *Semin. Thromb. Hemostatis* 13:36–49 (19B7).

The term "interferon" as used herein refers to the alpha, beta and gamma forms of human interferon, unless otherwise specified, whether it is isolated from a human source, or prepared by using a recombinant DNA system for expressing an interferon protein. For example, the preparation of a recombinant human interferon gamma and methods for determining the specific activity of the prepared composition are known in the art. See, for example, Gray et al., *Nature*, 295:503–508 (1982) and Lotz et al., *J. Immunol.*, 136:3636–3642 (1986). Recombinantly produced interferon is also available from commercial vendors such as Genentech (San Francisco, Calif.) and Amgen (Thousand Oaks, Calif.).

In addition, the preparation of human interferons alpha and beta and methods for determining the specific activity of the prepared compositions are well known. See, for example Zoon et al., *Proc. Natl. Acad. Sci., USA*, 76:5601–5606 (1979); Knight et al., *Science*, 207:525–526 (1980); Stein et al., *Proc. Natl. Acad. Sci., USA*, 77:5716–5719 (1980); Armstrong, *Appl. Microbiol.*, 21:723–725 (1971); Havell et al., *Antimicrob. Agents and Chemother.*, 2:476–484 (1972); and Gray et al., supra. The preparation of recombinant human interferon alpha and beta are also well known. See Goeddel et al., *Nucleic Acids Res.*, 8:4057–4073 (1980) and Hitzeman et al., *Nature*, 293:717–722 (1981), for exemplary methods of recombinant production of human interferon alpha and beta, respectively.

Recombinantly produced human interferon alpha is also available from commercial vendors such as Schering Corp. (Madison, N.J.), Amgen, Roche Laboratories (Nutley, N.J.) and Boehringer Mannheim (Indianapolis, Ind.). Recombinantly produced human interferon beta is also available from commercial vendors such as Cetus (Emeryville, Calif.).

The phrases "C1 inhibitor concentration-increasing amount" and "therapeutically effective amount", refer to an amount of interferon or IL-6 sufficient to measurably increase the subject's intravascular C1 inhibitor concentration, preferably by at least about 10 percent, more preferably by at least about 50 percent and most preferably at least about 100 percent. The interferon and/or IL-6 is typically administered as a pharmaceutical composition in the form of a solution or suspension. However, as is well known, both interferon and IL-6, either alone or in admixture, can also be formulated for therapeutic administration as a tablet, pill, capsule, aerosol, sustained release formulation or powder.

The preparation of therapeutic compositions containing interferon and/or IL-6 as active ingredients is well understood in the art. Typically, such compositions are prepared as injectables, either as liquid solutions or suspensions, however, solid forms suitable for solution in, or suspension in, liquid prior to injection can also be prepared. The preparation can also be emulsified. The interferon and/or IL-6 is often mixed with inorganic and/or organic excipients which are pharmaceutically acceptable and compatible with the active ingredient (interferon and/or IL-6). Suitable excipients are, for example, water saline, dextrose, glycerol or the like and combinations thereof. In addition, if desired, the composition can contain minor amounts of pharmaceutically acceptable auxiliary substances such as wetting or emulsifying agents, pH buffering agents which enhance the effectiveness of the active ingredient.

As used herein, the phrase "pharmaceutically acceptable" refers to molecular entities and compositions that do not produce an allergic or similar untoward reaction, such as gastric upset, dizziness and the like, when administered to a human.

The interferon and/or IL-6 is conventionally administered subcutaneously, as by injection of a unit dose, for example. The term "unit dose" as used herein refers to physically discrete units suitable as unitary dosages for humans, each unit containing a predetermined quantity of interferon and/or IL-6 calculated to produce the desired therapeutic effect in association with the required excipient.

The interferon is administered in a manner compatible with the dosage formulation, and in a therapeutically effective amount. Contemplated methods of administration include injection, infusion, implant and the like. The quantity to be administered depends on the subject's ability to use the interferon and/or IL-6, and the increase in the blood concentration of C1 inhibitor desired. Precise amounts of interferon and/or IL-6 required to be administered depend on the judgment of the practitioner and are peculiar to each individual. However, suitable interferon dosage ranges are of the order of $1 \times 10^6$ international units (IU) to $10 \times 10^6$ IU per square meter (M$^2$) of body surface area per day, preferably $1 \times 10^6$ IU to $4 \times 10^6$ IU/M$^2$ body surface area per day, and depend on the route of administration. Suitable IL-6 dosage ranges are of the order of $1 \times 10^4$ to $1 \times 10^6$ IU/M$^2$ body surface area per day, preferably about $1 \times 10^5$ to $6 \times 10^5$, and more preferably about $3 \times 10^5$ IU/M$^2$ body surface area.

As is well known in the art, the phrase "international unit" (also known in the art as "international reference unit"), when used in reference to interferon is a measure of the ability of an interferon preparation to inhibit cytopathic effect due to viral infection in an internationally standardized assay. The amount of international units present in a given preparation of interferon described herein is determined by comparison of the activity in that preparation to the activity present in an international standard sample of the same form of interferon available from the National Institute of Allergy and Infectious Diseases (NIAID), Research Resources Branch (Bethesda, Md, 20205) when measured by a method such as that described by Lotz et al., *J. Immunol.* 136:3036–3642 (1986).

Substantially pure interferon gamma preparations typically display an activity of about $20 \times 10^6$ IU per milligram (mg) of interferon protein. Therapeutically effective unit doses of interferon gamma are therefore in the range of about 5 micrograms (ug) to about 0.5 mg, preferably about 50 ug to about 200 ug, per M$^2$ of body surface area per day.

Substantially pure interferon alpha or interferon beta preparations each typically display an activity of about $2 \times 10^8$ IU per mg of interferon protein. Therapeutically effective unit doses of either of these forms of interferon are therefore in the range of about 0.5 ug to about 50 ug, preferably about 5 ug to about 20 ug, per M$^2$ of body surface area per day.

A therapeutically effective amount of interferon can also be expressed as a plasma concentration. For example, in preferred embodiments of the present invention, interferon is administered to achieve an intravascular plasma concentration in the range of about 0.5 IU to about 500 IU per ml, preferably about 10 IU to about 50 IU per ml.

Interleukin 6 or IL-6 refers to human interleukin 6, whether it is isolated from a human source, or prepared by using a recombinant DNA system for expressing an IL-6 protein. The preparation of isolated IL-6 and methods for determining the specific activity of the prepared composition are known in the art. See, for example, Muraguchi et al., *J. Immunol.*, 127:412–416 (1981), in which IL-6 is referred to as T-cell replacing factor, or TRF. Isolated IL-6 is also available from commercial vendors such as Genzyme (Boston, Mass.) and Amgen (Thousand Oaks, Calif.).

A measure of the amount of IL-6 to be used in the present invention is expressed in international units (IU). One IU of IL-6 is that amount that gives 50 percent maximal stimulation of IgG secretion by the human lymphoblastoid cell line CESS when measured after 4 days of culturing $5 \times 10^3$ CESS cells in 200 microliters of culture medium in a well of a 96-well microtiter culture plate as described by Muraguchi et al., *supra*. CESS cells may be obtained from the American Type Culture Collection (ATCC; Rockville, Md.) and have the accession number TIB 190.

Methods for determining the concentration of C1 inhibitor in plasma are well known in the art, a preferred method being that described in Example 3. Typical methods include an enzyme-linked immunosorbent assay (ELISA) described by Lotz et al., *J. Immunol.*, 139:3382–3387 (1987), and a rocket immunoelectrophoresis (RIE) assay described by Nitsche et al., *Am. J. Clin. Pathol*, 75:679–684 (1981). Anti-C1 inhibitor antibody preparations suitable for use in the above methods to determine C1 inhibitor concentrations in plasma may be prepared by standard immunologic techniques using purified C1 inhibitor protein, such as described in Example 2, or may be obtained from commercial sources.

In another embodiment, the present invention contemplates a therapeutic method in which a patient's blood is exposed to a contact system activating surface such as, for example, as occurs when blood is circulated through a prosthetic device. The method includes administering a C1 inhibitor intravascular (blood) concentration-increasing amount of interferon, preferably interferon gamma, and more preferably interferon gamma in combination with interferon alpha and/or interferon beta. Administration of the interferon is performed substantially concurrently with exposing the patient's blood to the contact system activating surface, such as, for example, exposing the patient's blood to a prosthetic surface on a prosthetic device.

"Prosthetic device" refers to a biologic or synthetic vascular prosthesis that is inserted into the vasculature so as to facilitate the transport of blood from one point in a patient's vasculature to another. A "prosthetic surface", or "luminal surface", is that part of a prosthetic device which is exposed to and in contact with the transported blood.

Prosthetic devices having a surface exposed to a patient's blood when operatively inserted into a patient's circulatory system are well known in the art. See, "Biological and Synthetic Vascular Prostheses," J. Stanley, ed., Grune and Stratton, N.Y. (1982).

Typical prosthetic devices include arterial protheses, arterial stents, artificial hearts, artificial heart valves, arterial-venous shunts, ex vivo therapeutic devices, and the like. Arterial-venous shunts are typically sections of non-endothelialized tubing, usually constructed of a polymeric material, that are used to transport arterial blood to a vein, either directly or first through an ex vivo prosthetic device. Exemplary ex vivo prosthetic devices include hemodialysis devices, cardiopulmonary bypass devices, and the like. In preferred embodiments, interferon administration is performed prior to exposing the patient's circulating blood to a contact activating surface, preferably while the intravascular concentration of C1 inhibitor is increased at least about 10 percent, preferably at least about 50 percent and more preferably at least about 100 percent when compared to its concentration prior to the administration of interferon gamma. However, methods wherein administration of the therapeutically effective amount of interferon and exposure of the patient's circulating blood to the contact activating surface are performed substantially concurrently and wherein exposure is performed prior to administration, are also contemplated.

By "substantially concurrently" if is meant that administration of the interferon and/or IL-6 occurs within a time period of between 240 hours before, preferably 120 hours before, and 72 hours after the patient's blood is first exposed to the contact activating surface. However, in preferred embodiments, administration of the interferon is performed within a time period of 4 to 48 hours, preferably 8 to 24 hours, prior to exposing the patient's blood to the contact activating surface or performing invasive surgery. In other preferred embodiments, the patient is given serial administrations of interferon and/or IL-6 at about 24 hour intervals, such as at 72, 48 and 24 hours, before exposing the patient's blood to a contact activating surface or performing invasive surgery.

Administration of a therapeutically effective amount of interferon, preferably interferon gamma, is also an effective treatment for a clinical symptom in a patient due to a C1 inhibitor deficiency. Methods for diagnosing the presence of C1 inhibitor deficiency in a patient (human subject) are well known in the art. See Kalter et al., *J. Infect. Dis.*, 151:1019-1027 (1985). Those methods include direct measurements of plasma C1 inhibitor concentrations by the ELISA and RIE methods described herein.

Alternatively, indirect methods may indicate to the diagnosing physician the presence of C1 inhibitor deficiency. For example, the blood of patients having acquired C1 inhibitor deficiency contains decreased or undetectable levels of the complement components C1q, C1, C4 and C2. Davis et al., *Ann. Rev. Immunol.*, 6:595-628 (1988). Therefore assays that measure the levels of these complement components in the blood have the capability to indicate the presence of a deficiency in C1 inhibitor.

In addition, a C1 inhibitor deficiency can be indicated by the symptoms clinically presented by a patient. For example, patients with hereditary angioedema exhibit characteristic symptoms known to be caused by a genetic deficiency of C1 inhibitor. For a description of those symptoms, see Gelfand et al., *Medicine*, 58:321-328 (1979); and Frank et al., *Ann. Int. Med.*, 84:580-593 (1976).

Administration of a C1 inhibitor concentration-increasing amount of interferon is also a therapeutically effective adjunct to performing invasive surgery. The term "invasive surgery" as used herein does not include the mere puncture of the patient's skin, e.g., by a hypodermic needle, without an attendant medical procedure being performed substantially concurrently therewith.

Exemplary attendant medical procedures are invasive surgical procedures that penetrate the dermis and expose the patient's blood and other bodily fluids and tissues to foreign materials, devices, prostheses, catheters and the like. Such surgical procedures include but are not limited to hemodialysis, cardiopulmonary bypass, catheterizations such as angioplasty, arterial balloon assistance and organ transplant.

In one embodiment the contemplated in invasive surgical procedure is the infusion, such as by catheterization, of radiographic contrast media (RCM) for diagnostic purposes. It is reported that RCM infusions result in complement system activation [Arroyave et al., *J. Immunol.*, 117:1866-1869 (1976); Fareed et al., *Sem. Thromb. Hemostasis*, 10:306-328 (1984)]and contact system activation [Zuraw et al., *Allerg. Clin. Immunol.*, 81:223, A218 (1988)]. Thus, this embodiment contemplates the administration of a C1 inhibitor concentration-increasing amount of interferon as an adjunct to performing a RCM infusion.

The present invention further contemplates pharmaceutical compositions, preferably sterile and preferably containing a pharmaceutically acceptable excipient, that can be administered, with or without dilution, to produce a C1INH concentration increase, preferably at least a 10% increase, in a human subject. One such composition contains interferon gamma admixed in a pharmaceutically acceptable excipient with interferon alpha and/or interferon beta wherein interferon is the only biologically active ingredient. Preferably each interferon is present at a concentration of at least about 10,000 IU/ml, preferably at least about 100,000 IU/ml.

Another pharmaceutical composition of the present invention contains IL-6 in combination (admixture) with interferon, preferably interferon gamma, wherein interferon and IL-6 are the only biologically active ingredients and both are present in at least a concentration that permits therapeutic administration. In preferred embodiments, the IL-6 and each interferon present are present at a concentration of at least about 10,000 IU/ml, preferably at least about 100,000 IU/ml. (1980); Armstrong, *Appl. Microbiol.*, 21:723-725 (1971);

EXAMPLES

The following examples are intended to illustrate, but not limit, the present invention.

1. Isolation of C1 Inhibitor Protein

To 400 milliliters (ml) of citrated plasma were admixed the following to produce the final concentrations indicated in the parenthesis: aprotinin (333IU/ml) benzamidine (0.1 mg/ml), 1,10-phenanthroline (0.01mM), and phenylmethylsulfonyl fluoride (1mM). C1INH protein was then isolated from the plasma mixture according to the methods of Salvesen et al. *J. Biol. Chem.*, 260:2432-2436 (1985), which disclosure is hereby incorporated by reference, to form about 5 mg of purified C1INH protein that migrates as a substantially pure band of about 110,000 daltons in molecular weight when analyzed by polyacrylamide gel electrophoresis in the presence of sodium dodecylsulphate (SDS-PAGE).

2. Preparation of Anti-C1INH Antibodies

Goats were immunized using the purified C1INH protein prepared as described in Example 1 by using techniques well known in the art. The resulting goat antisera was harvested to form anti-human C1INH antisera.

Immunoglobulin IgG was isolated from the antisera by precipitation with ammonium sulphate. A 40% ammonium sulphate precipitate was prepared and the precipitated IgG antibodies were recovered to yield anti-C1INH IgG antibodies.

Purified C1INH protein, prepared as described in Example 1, was conjugated to CNBr-Sepharose 4B (Pharmacia Fine Chemicals, Upsala, Sweden) using amounts and methods recommended by the manufacturer to form Sepharose-conjugated inhibitor. The anti-C1INH IgG antibodies were admixed with the Sepharose-conjugated inhibitor and maintained for a time period sufficient to form a antibody-inhibitor complex. Anti-C1INH antibodies present in the antibody-inhibitor complex were then recovered by subsequent recommended treatment of the Sepharose conjugate containing bound complex to produce affinity-purified anti-C1INH antibodies.

3. Secretion of C1 Inhibitor by Liver Cells In Vitro

A. Detection of C1 Inhibitor Produced By Interferon Treated Hepatoma Cell Lines

Human hepatoma cell lines HepG2, Hep3B and Alexander PLC obtained from the American Type Culture Collection (HB 8065, HB 8064 and CRL 8024, respectively; ATCC, Rockville, Md.) were each cultured in RPMI 1640 medium containing 10% fetal bovine serum, L-glutamine, and antibiotics. When the cultures of these cell lines reached confluency, the culture media was removed, fresh media containing from 0.01 to 10 IU/ml of interferon gamma was added to each culture. A sample of medium (culture supernatent) was harvested from each culture at the various time points indicated in FIG. 1 and were frozen at minus 20 degrees C. The amount of C1 inhibitor in the harvested medium samples was then determined using the enzyme-linked immunosorbent assay (ELISA) described below.

About 100 microliters (ul) of a coating solution containing affinity purified goat anti-human C1INH antibody, prepared as described in Example 2 and at a concentration of 2.5 micrograms (ug) per ml of phosphate buffered saline solution (PBS), were added to the wells of flat-bottom 96-well microtiter plates (Immulon 2; Dynatech Laboratories, Chantilly, Va.). The plates were then maintained for 6 hours at 4 degrees C to permit the antibodies to adsorb onto the walls of the wells. The coating solution was then removed by inversion and shaking.

About 100 ul blocking solution [5 mg/ml bovine gamma globulin, 1 mg/ml bovine serum albumin (BSA), 1 mg/ml gelatin in PBS containing 0.05% Tween 20] was added to each well. The blocking solution was maintained in the wells for 16 hours at 4 degrees C to block excess protein binding sites and then removed by inversion and shaking. The wells were then washed with a wash solution (PBS containing 0.05% Tween 20) three times to remove any unbound protein.

Two hundred ul of harvested medium sample, diluted 9:1 in serum buffer [0.01M phosphate buffer containing 1 mg/ml gelatin, 0.82% NaCl, 0.1 mg/ml thimerosal, 1 mg/ml BSA, and 0.05% Tween 20] was added to the blocked wells to form immunoreaction admixtures. The wells were then maintained for 16 hours at 4 degree C to allow an immunoreaction to occur. Thereafter the harvested medium sample was removed from the immunoreacted wells by inversion and shaking and the wells were washed three times as before.

A monoclonal anti-C1INH antibody was prepared as described by Zuraw et al., *J. Allergy. Clin. Immunol.*, 73:155 (1984). About 100 ul of a solution containing monoclonal anti-C1INH antibody at a concentration of 2 ug/ml . in anti-Ig buffer [0.01 M phosphate buffer containing 0.82% NaCl, 0.1 mg/ml thimerosal, 5 mg/ml BSA, and 0.05% Tween 20] were admixed to each immunoreacted well, and the wells were maintained for 3 hours at room temperature with shaking. The monoclonal antibody solution was then removed by inversion and shaking and the wells were washed three times as before.

About 100 ul of a solution containing goat anti-mouse IgG horseradish peroxidase conjugate (Cal Tag Laboratories, S.F., Calif.) diluted 1:4000 in anti-Ig buffer was added to each well and the wells were maintained at room temperature for 2 hours with shaking. Thereafter the horseradish peroxidase conjugate was removed by inversion and shaking and the wells were then washed three times as before, followed by two washes with PBS.

About 100 ul of a chromogenic substrate solution containing 2,2'-azido-di-3-ethylbenzthiazoline-6-sulfonic acid (Sigma Chemical Co., St. Louis, Mo.) at a concentration of 1 mg/ml in buffer solution (94 mM $Na_2HPO_4$, 53 mM citric acid, pH 4.6, 0.005% $H_2O_2$) was added to each well and the wells were maintained for 20 to 60 minutes at room temperature with shaking to allow a color-forming reaction product to occur. The optical density of the solution in each well was then read with a MR600 Microplate Reader (Dynatech, Alexandria, Va.) to determine the amount of C1INH-containing immunoreaction product formed and thereby provide a measure of the presence of C1INH in each culture medium sample.

The results of the above ELISA assay are shown in FIG. 1. The amount of C1INH detected is expressed as a concentration in nanograms (ng) per ml, calculated by comparison to the optical density values obtained for samples containing known amounts of purified C1INH protein. All ELISA measurements are expressed as the average of duplicate determinations. At all concentrations of interferon gamma tested, including 0.1 IU/ml and 0.01 IU/ml, the amount of C1INH secreted by the HepG2 cells was higher than the amount spontaneously secreted from unstimulated cultures. The results of this study demonstrate that the addition of interferon gamma to cultured HepG2 cells stimulated a dose dependent increase in the amount of C1INH secreted by the cells.

Figure 2:
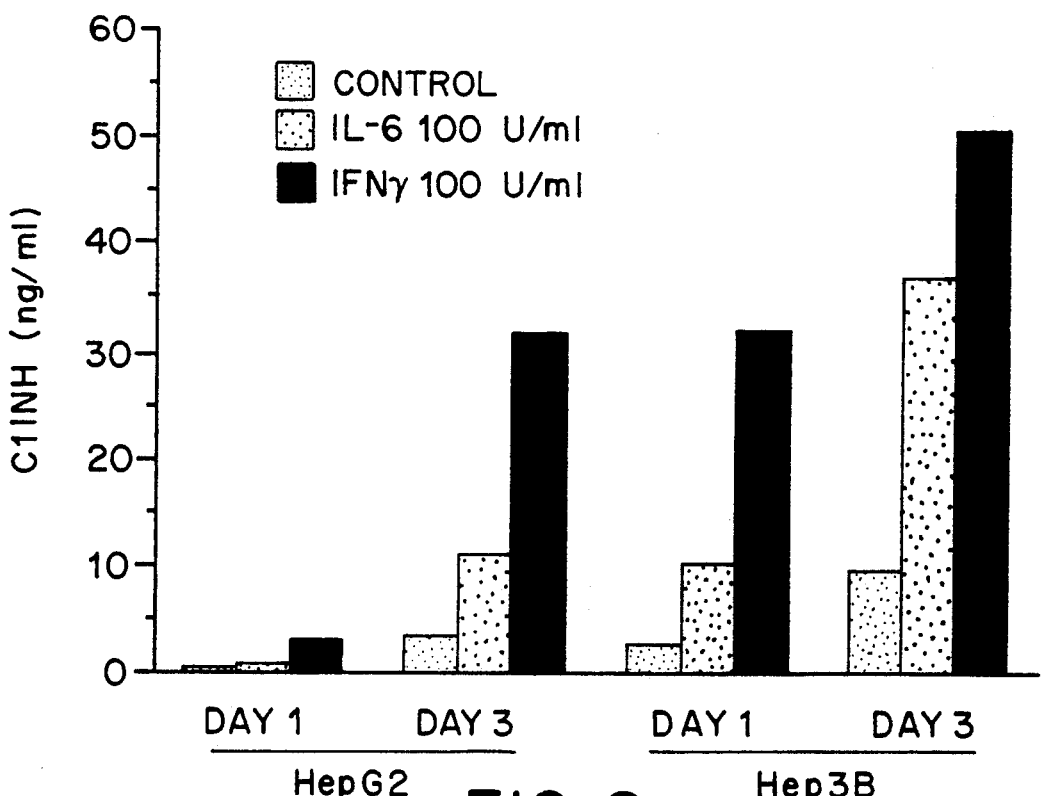
FIG. 2 is a bar graph illustrating that two different hepatoma cells lines increase C1INH secretion following interferon gamma stimulation. Both HepG2 and Hep3B cell lines, were cultured with 100 IU per ml (IU/ml) interferon gamma as described in Example 3A. A parallel set of cultures of HepG2 and Hep3B cells received interleukin -6 (IL-6) in place of interferon gamma. A control culture was also maintained that received no stimulation. Samples of culture supernatants were removed at day 1 and day 3 and the level of secreted C1INH in each culture supernatant was determined by ELISA assay and expressed as ng C1INH per ml media (ng/ml).

Using harvested medium samples from interferon gamma stimulated Hep3B cells, similar results were obtained in the above ELISA assay. As shown in FIG. 2, interferon gamma increased the amount of C1INH secreted by Hep3B cells.

Using harvested medium samples obtained from Alexander PLC cells stimulated with interferon gamma, an increase in C1INH secretion was observed in the above ELISA assay. However, the level of C1INH secreted after culturing with interferon gamma at 100 IU/ml for 3 days produced a cumulative C1INH concentration of 136 ng/ml, in comparison to a constitutively produced level of 95 ng/ml when cultured in the absence of interferon gamma. These results demonstrate that both Hep3B cells and Alexander PLC cells increase secretion of C1INH when stimulated with interferon gamma.

B. Detection of C1 Inhibitor Produced by Hepatoma Cell Lines Treated with Interferon and IL-6

A similar but lower increase in C1INH secretion was stimulated both in Hep3B cells and in HepG2 cells when interleukin-6 (IL-6; obtained from Osaka University, Osaka, Japan) was added at 100 IU per ml to the cultures in place of the added interferon gamma as described in Example 3A. See FIG. 2.

Figure 3:
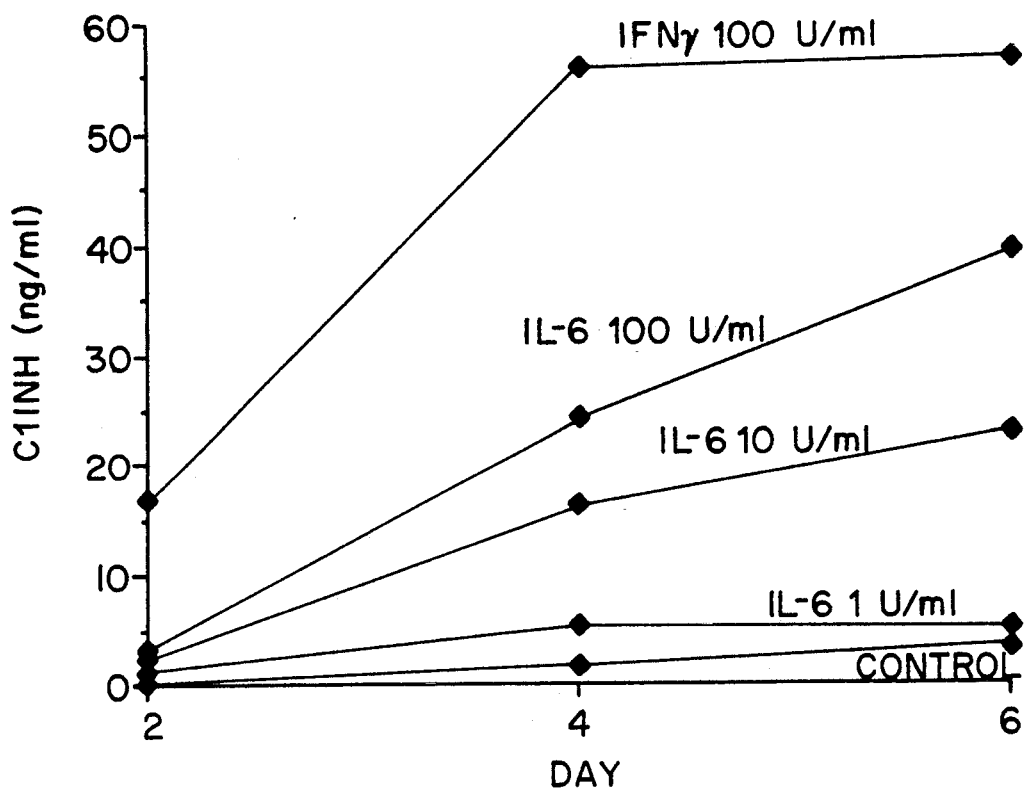
FIG. 3 is a graph illustrating the in vitro dose dependent effect of interleukin-6 (IL-6) stimulation on C1INH secretion. HepG2 cells were stimulated by addition to the culture medium of varying amounts, from no stimulant (Control) to 100 international unit per ml (U/ml), of IL-6 as indicated, or by addition of 100 international units per ml of interferon gamma (IFN), as described in Example 3B. Culture supernatant samples were removed at the days indicated and the level of secreted C1INH was determined by ELISA assay and expressed as ng/ml.

A dose-responsiveness for C1INH secretion by stimulation with IL-6 was also demonstrated by adding from 1 IU/ml to 10o IU/ml of IL-6 in place of interferon gamma to HepG2 cultures and measuring the secreted C1INH by the ELISA assay described in Example 3A. As shown in FIG. 3, IL-6 stimulates a dose dependant increase in the amount of C1INH secreted by HepG2 cells.

Figure 4:
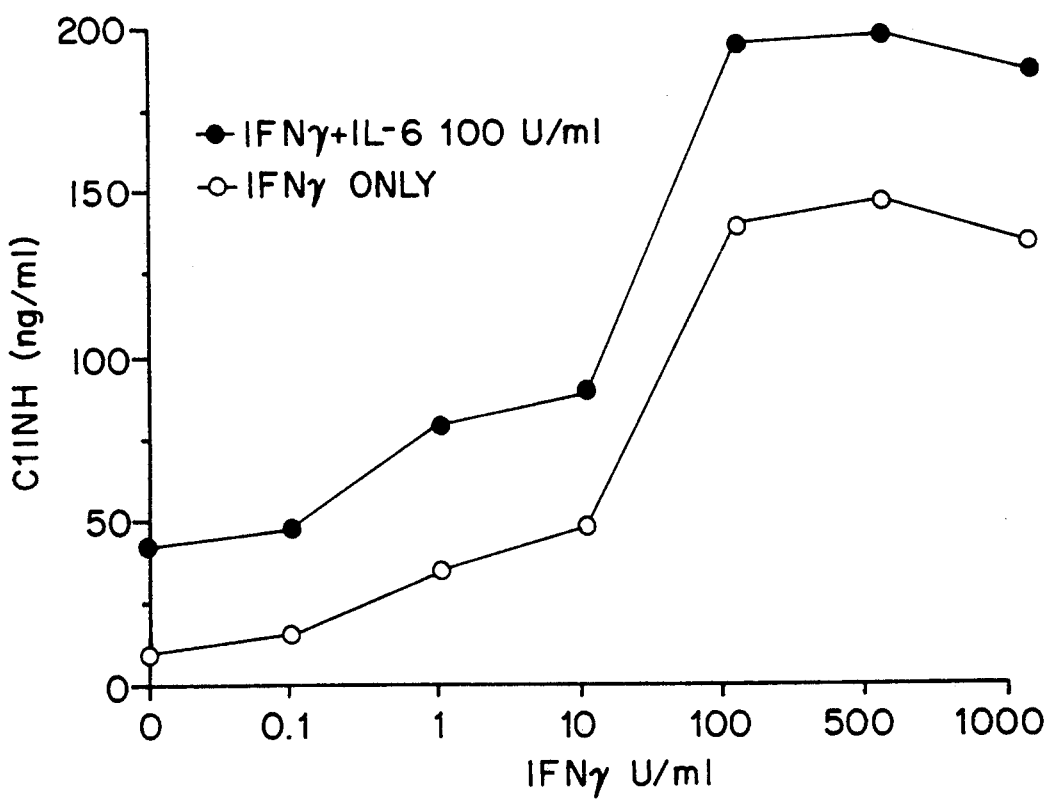
FIG. 4 is a graph illustrating the additive effect that a combination of interferon gamma plus IL-6 has upon the secretion of C1INH in vitro. HepG2 cells were cultured with interferon gamma at the concentrations indicated as international units per ml (U/ml). A parallel set of cultures of HepG2 cells received IL-6 at 100 international units (U/ml) in addition to the added interferon gamma. Both sets of resulting culture supernatant samples were removed after 6 days and the level of secreted C1INH was determined by ELISA assay as described in Example 3B and expressed as ng C1INH per ml (ng/ml).

An additive effect on C1INH secretion was produced by the simultaneous administration of both interferon gamma and IL-6 to a culture of HepG2 cells. Following the procedure in Example 3A for stimulating HepG2 cells, cell cultures were stimulated with fresh media containing both (1) various amounts of interferon gamma from 0 to 1000 IU per ml and (2) a constant amount of IL-6 at 100 IU per ml. The amount of C1 inhibitor in the harvested medium samples was then determined using the ELISA assay described in Example 3A. As shown in FIG. 4, the results indicate that added IL-6 increases the level of C1 inhibitor secretion by a relatively constant amount of about 40 ng per ml independent of the dosage of interferon gamma.

Thus, in preferred embodiments, the methods of the present invention include administering a C1 inhibitor concentration-increasing amount of IL-6 in conjunction with administration of the therapeutically effective amount of interferon.

C Detection of C1 Inhibitor Produced By Primary Human Hepatocytes Treated With Interferon or Other Cytokines Primary human hepatocytes were isolated from a fresh liver biopsy, and primary cultures were established. The cultures were then stimulated with various cytokines and culture supernatants were harvested after the cultures were maintained for the times indicated in Table 1. The amount of C1 inhibitor secreted into each culture supernatant was then determined using the ELISA described in Example 3A. The results of this study are shown in Table 1 and indicate that C1INH was secreted by interferon gamma stimulated primary hepatocytes after about 44 hours and thereafter the hepatocytes was stimulated by IL-6 and by tumor necrosis factor alpha (TNF).

TABLE 1

C1INH Secretion by Primary Human Hepatocytes In Vitro[1]

| Stimulus[2] | C1INH Secretion | | | | |
|---|---|---|---|---|---|
| | 11 hr | 18 hr | 44 hr | Day 3 | Day 4 |
| None | 0 | 0 | 0 | 0 | 0 |
| IFN | 0 | 0 | 1.07 | 1.51 | 3.98 |
| IL-6 | 0 | 0 | 0 | 0.45 | 0.69 |
| LPS | 0 | 0 | 0 | 0 | 0 |
| IL-1 | 0 | 0 | 0 | 0 | 0 |
| TNF | 0 | 0 | 0 | 0.42 | 1.21 |

[1]C1INH secretion by primary hepatocytes is expressed as a protein concentration in ng/ml.
[2]IFN indicates interferon gamma added at 50 IU/ml. IL-6 indicates interleukin-6 added at 50 IU/ml. LPS indicates lipopolysaccharide (Sigma) added at 100 ng/ml. IL-1 indicates interleukin-1 obtained from Dr. C. Dinarello (Tufts University, Boston, MA), added at 20 ng/ml. TNF indicates tumor necrosis factor alpha, obtained from Dr. H. Shepard (Genentech), added at 20 ng/ml.

D. Radioimmunoprecipitation of C1 Inhibitor

Control and 100 IU/ml interferon gamma treated HepG2 cells, cultured as described in Example 3A, were washed three times with PBS to remove the culture medium. Both cultures were then further cultured in methionine free culture medium containing 2% FBS and 40 uCi/ml $^{35}$S-methionine (NEG-009T, New England Nuclear, Boston, Mass.) for 24 hours. Thereafter, the medium was collected and centrifuged, and the labeled culture supernatant was retained.

A sample of the monoclonal anti-C1INH antibody, prepared as described in Example 3A was conjugated to Sepharose 4B beads (Pharmacia) using methods recommended by the manufacturer. One hundred or two hundred fifty ul of labeled culture supernatant was admixed with 40 ul of a 50% (v/v) suspension of the Sepharose-conjugated beads in phosphate buffered saline (PBS), and maintained for 1 hour at room temperature with continuous gentle shaking on a Tommy MT-300 to form immunoreacted beads. (Peninsula Laboratories, Belmont, Calif.).

Following this immunoreaction, the beads were then washed 10 times with PBS-Tween (PBS containing 0.05% Tween 20) to remove all non-absorbed proteins. The beads were then resuspended in sample buffer [0.0625 M Tris, pH 6.8, 3% SDS, 10% glycerol, and bromophenol blue], and the resuspended beads were maintained for in a boiling waterbath for 5 minutes. The resuspended beads were then centrifuged and the resulting supernatants were retained. The supernatants were then applied to 7.5% polyacrylamide slab gels and electrophoresed according to the methods of Laemmli et al., Nature, 227:680-685 (1970), to separate the immunoabsorbed proteins. Following electrophoresis, the gels were dried to remove excess moisture and exposed to X-ray film to form autoradiographs.

Figure 5:
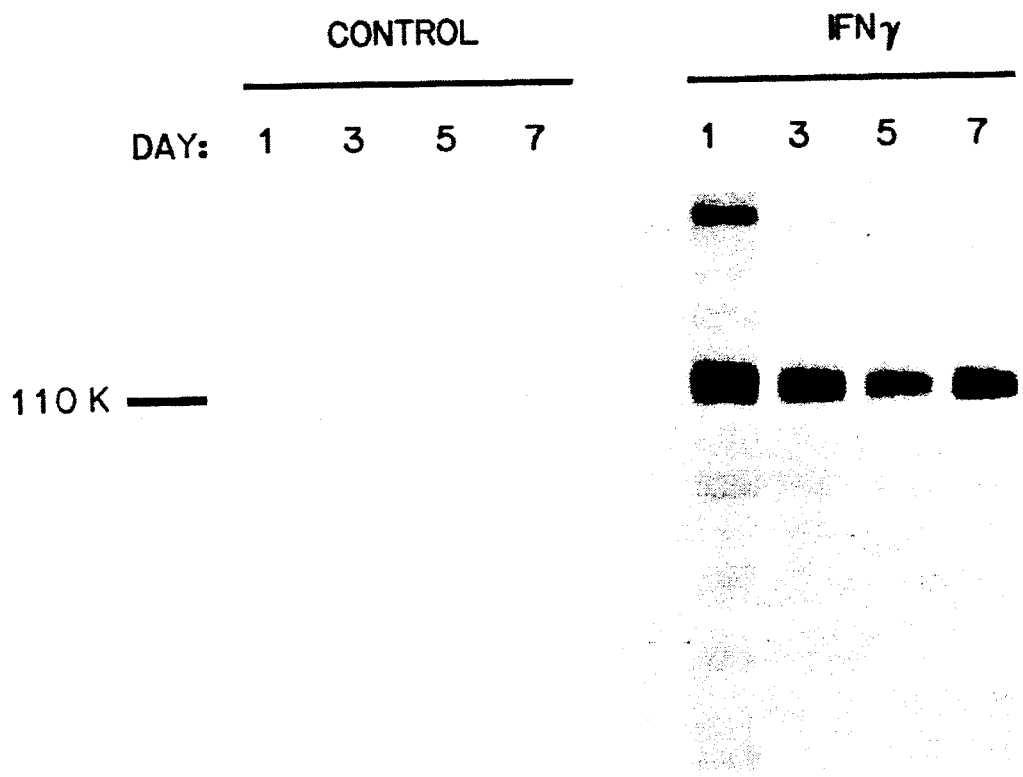
FIG. 5 is an autoradiograph illustrating that C1INH is synthesized in vitro following interferon gamma stimulation as described in Example 3B. HepG2 cells were cultured with interferon gamma at 100 IU/ml (IFN) or without any interferon gamma (control) and were labeled in culture with $^{35}S$-methionine for 24 hours. Thereafter, the culture supernatants were harvested and immunoreacted with monoclonal anti-C1INH conjugated Sepharose 4B beads. The proteins present on the immunoreacted beads were then electrophoresed on 7.5% polyacrylamide gels and visualized by autoradiography. The labeled C1INH protein migrates as a band at about 110 kilodaltons (K) in molecular weight.

The resulting autoradiographs are shown in FIG. 5 and demonstrate that C1INH migrating as a protein of about 110 kilodaltons (K) in molecular weight, was secreted by HepG2 cells treated with a C1 inhibitor increasing amount of interferon gamma. Although control cells were found to secrete a very low level of C1INH, detectable only after 7 days, the interferon gamma-treated cells secreted C1INH in large amounts after less than 24 hours of treatment. This data indicates that interferon gamma stimulates HepG2 cells to synthesize C1INH in vitro.

4. Serum C1INH Levels in Patients with Acute Phase Response

Serum from 38 patients was obtained and each was screened by the routine and standardized clinical laboratory procedure called the Serum Protein Electrophoresis Profile (SPEP). Nineteen of the SPEP screened sera exhibited increased alpha$_1$-proteinase inhibitor indicative of a classic acute phase response and the remaining 19 sera exhibited normal alpha$_1$-proteinase inhibitor levels.

These same 38 sera were also screened to determine their C1INH levels by the rocket immunoelectrophoresis (RIE) procedure described by Nitsche et al., Amer. J. Clin. Path., 76:5 (1981). Anti-C1INH IgG antibodies prepared as described in Example 2 were diluted 10:1 in barbital buffer [0.04 M barbital, 0.05% sodium azide, 10 mM ethylenediaminetetraacetic acid (EDTA), pH 8.6] and admixed 1:1 with a 1.8% (w/v) agarose solution in barbital buffer to form antibody containing agarose plates according to the methods of Nitsche et al. (supra). A patient's serum sample was diluted 3:1 in barbital buffer, ten ul of the diluted sample was added to punched wells in the antibody-agarose plates and the sample was electrophoresed The area contained with the resulting precipitant arc (rocket) on the electrophoresed RIE plate was determined by planimetry using a model L-20 compensating polar planimeter (Los Angeles Scientific Instrument Company, Los Angeles, Calif.).

The concentration of C1INH in a serum sample was then determined from the rocket area measurement by comparison to the rocket area obtained using a serial dilution of a solution containing known amounts of purified C1 inhibitor prepared as described in Example 1. The mean level of C1INH was significantly greater for the average of the 19 sera from patients with an acute phase response (average [C1INH] equals 35.1±5.6 mg/deciliter [dl]) when compared to the mean level of C1INH determined for the average of the 19 normal sera ([C1INH] equals 26.3±4.1 mg/dl.

These results indicate that C1INH protein levels correlate with alpha$_1$-proteinase inhibitor levels. Because alpha$_1$-proteinase inhibitor is a major component of acute phase response, this correlation indicates that C1INH is itself an acute phase protein.

5. In Vivo Increases of C1 Inhibitor by Administration of Interferon gamma

Patients with chronic granulomatous disease (CGD) received 2 million IU of recombinant interferon gamma (Genentech) by subcutaneous injection at 24 hour intervals. Plasma samples were obtained from the patients immediately prior to the first injection and also at the times indicated in Table 2 after he first injection. Plasma samples were also obtained from a control donor who received no injections.

Plasma samples obtained from one of the CGD patients (Patient A) and from a control donor were then analyzed to determine the concentration of C1INH using rocket immunoelectrophoresis (RIE) as described in Example 4 except that undiluted plasma samples were added to the punched wells of the diluted serum samples.

The results of an RIE analysis of patient A and the control donor's plasma are shown in Table 2.

TABLE 2

| RIE Analysis of the Effect of Interferon Gamma On C1 Inhibitor In Vivo | | |
|---|---|---|
| Sampling | Plasma Levels of C1INH[1] | |
| Time | Patient A | Control |
| Before[2] | 100 | 237 |
| 18 hour | 137 | 251 |
| 48 hour | 166 | 231 |
| 120 hour | 199 | NT[2] |

[1]Plasma levels are expressed as a percentage of the amount detected in patient A at the "before" sampling time.
[2]"Before" indicates that the sample was obtained immediately prior to the first injection with interferon gamma.
[3]N.T. indicates sample not tested.

As can be seen from Table 2, plasma C1INH levels for patient A continually rose following the injections while the level of C1INH in the control donor's plasma remained relatively constant. The results demonstrate the patient's in vivo ability of interferon gamma to increase intravascular concentration of C1INH.

The plasma samples from CGD patients were also analyzed for C1INH by the ELISA assay described in Example 3A, except that the plasma samples were first diluted 8,000:1 in serum buffer before being added to the blocked wells. The results of the ELISA analysis of GCD patient's plasma samples are shown in Table 3.

TABLE 3

| ELISA Analysis of the In vivo Effect of Interferon Gamma on Intravascular C1INH | | | |
|---|---|---|---|
| Sampling | Patient Plasma Levels of C1INH[1] | | |
| Time | A[3] | B | Control |
| Before[2] | 98 | 103 | 140 |
| 14 hour | | 177 | |
| 1 day | 105 | | 193 |
| 3 day | 106 | | |
| 4 day | 150 | | |
| 7 day | | | 129 |

[1]The data is expressed as the concentration in ug/ml of C1INH present in the plasma.
[2]"Before" indicates that the sample was obtained immediately prior to the first injection with interferon gamma.
[3]"A" is the same patient receiving the same course of interferon gamma therapy as described in Table 2.

The results demonstrate that following the administration of interferon gamma by subcutaneous injection the intravascular C1INH increased in the CGD patients.

Four patients with rheumatoid arthritis were given 2 million IU of recombinant interferon gamma (Amgen) once a week by subcutaneous injection. Plasma samples were drawn from the patients immediately prior to the first injection and were also drawn at about 2 to 4 weeks after the first injection depending on the patient. Plasma samples were then analyzed by RIE as described above for the CGD patient's plasma.

Results obtained using plasma samples from the four rheumatoid arthritis patients are shown in Table 4.

TABLE 4

| RIE Analysis of the In Vivo Effect of Interferon Gamma on C1 Inhibitor in Rheumatoid Arthritis Patients | | | | |
|---|---|---|---|---|
| Sample | Plasma Levels of C1INH[1] | | | |
| Time | A | B | C | D |
| Before[2] | 1.546 | 1.438 | 1.053 | 1.381 |
| After[3] | 2.134 | 1.703 | 1.702 | 1.689 |

[1]The numbers indicate the surface area of an RIE rocket as measured by a planimeter for plasma samples obtained from patients A through D at the times indicated.
[2]"Before" indicates that the sample was taken immediately prior to injection with interferon gamma.
[3]"After" indicates that the sample was taken at 2 or 4 weeks after the first injection of interferon gamma depending on the patient.

The results indicate that all patients treated by subcutaneous injection with interferon gamma exhibited an increase in intravasular C1 inhibitor concentrations.

The foregoing is intended as illustrative of the present invention but not limiting. Numerous variations and modifications may be effected without departing from the true spirit and scope of the invention.

What is claimed is:

1. A method of treating blood trauma characterized by activation of the complement or contact system, or both, in a patient, comprising administering a therapeutically effective amount of interferon gamma to said patient, wherein said effective amount is an amount sufficient to raise the C1 inhibitor concentration in the blood of said patient at least 10 percent.

2. The method of claim 1 wherein said amount of interferon gamma is administered by subcutaneous injection and is in the range of $1 \times 10^6$–$4 \times 10^6$ IU per M$^2$ of body surface area of said patient.

3. The method of claim 1, wherein said effective amount comprises an amount sufficient, to produce an intravascular plasma concentration of interferon gamma in the range of about 0.5 IU/ml to 500 IU/ml.

4. The method of claim 3, wherein said effective amount comprises an amount sufficient to produce an intravascular plasma concentration of interferon gamma in the range of about 10 IU/ml to 50 IU/ml.

5. A method of increasing the intravascular concentration of C1 inhibitor in a patient exhibiting a clinical symptom of C1 inhibitor deficiency, which method comprises administering to the patient a therapeutically effective amount of interferon gamma, wherein said effective amount is an amount sufficient to raise the C1 inhibitor concentration in the blood of said patient at least 10 percent.

6. The method of claim 5 wherein said amount of interferon gamma is administered by subcutaneous injection and is in the range of $1 \times 10^6$–$4 \times 10^6$ IU per $M^2$ of body surface area of said patient.

7. The method of claim 5, wherein said effective amount comprises an amount sufficient to produce an intravascular plasma concentration of interferon gamma in the range of about 0.5 IU/ml to 500 IU/ml.

8. The method of claim 7, wherein said effective amount comprises an amount sufficient to produce an intravascular plasma concentration of interferon gamma in the range of about 10 IU/ml to 50 IU/ml.

* * * * *